United States Patent
Barbour et al.

(10) Patent No.: US 9,724,489 B2
(45) Date of Patent: Aug. 8, 2017

(54) SELF-REFERENCING OPTICAL MEASUREMENT FOR BREAST CANCER DETECTION

(71) Applicant: The Research Foundation for The State University of New York, Albany, NY (US)

(72) Inventors: Randall L. Barbour, Glen Head, NY (US); Rabah M. Al Abdi, Brooklyn, NY (US)

(73) Assignee: The Research Foundation for The State University of New York, Albany, NY (US)

( * ) Notice: Subject to any disclaimer, the term of this patent is extended or adjusted under 35 U.S.C. 154(b) by 141 days.

(21) Appl. No.: 14/397,305

(22) PCT Filed: Apr. 25, 2013

(86) PCT No.: PCT/US2013/038153
§ 371 (c)(1),
(2) Date: Oct. 27, 2014

(87) PCT Pub. No.: WO2013/163385
PCT Pub. Date: Oct. 31, 2013

(65) Prior Publication Data
US 2015/0119665 A1    Apr. 30, 2015

Related U.S. Application Data

(60) Provisional application No. 61/639,132, filed on Apr. 27, 2012.

(51) Int. Cl.
*A61B 6/00*    (2006.01)
*A61M 16/10*    (2006.01)
(Continued)

(52) U.S. Cl.
CPC .......... *A61M 16/10* (2013.01); *A61B 5/0073* (2013.01); *A61B 5/14552* (2013.01);
(Continued)

(58) Field of Classification Search
USPC .......................................... 600/476
See application file for complete search history.

(56) References Cited

U.S. PATENT DOCUMENTS

| | | |
|---|---|---|
| 2004/0039268 A1 | 2/2004 | Barbour et al. |
| 2005/0197583 A1* | 9/2005 | Chance ............... A61B 5/0073 600/476 |
| 2010/0292569 A1 | 11/2010 | Hielscher et al. |

OTHER PUBLICATIONS

Carpenter C.M. et al., "Inspired Gas-Induced Vascular Change in Tumors With Magnetic-Resonance-Guided Near-Infrared Imaging", Journal of Biomedical Optics 15(3):036026-1-036026-5 (May/Jun. 2010).
(Continued)

*Primary Examiner* — Joel F Brutus
(74) *Attorney, Agent, or Firm* — Scully, Scott, Murphy & Presser, P.C.

(57) ABSTRACT

Optical data is obtained from a pair of breasts, employing a simultaneous bilateral referencing protocol, and is subsequently analyzed employing a self-referencing data analysis method. Optical measurements can be performed on both breasts simultaneously under various protocols, including resting-state measures and evoked responses. Sensing hardware and data collection protocols are economical and can be implemented without patient discomfort. The natural variance inherently associated with optical measures of the breast is reduced by: imposition of substantially symmetric boundary conditions; collection of simultaneous bilateral dynamic measures; referencing measurement data of one breast to measurement data from another.

20 Claims, 9 Drawing Sheets

(51) Int. Cl.
    *A61B 10/00*     (2006.01)
    *A61B 5/00*      (2006.01)
    *A61B 5/1455*    (2006.01)
(52) U.S. Cl.
    CPC . *A61B 10/0041* (2013.01); *A61M 2205/3303* (2013.01); *A61M 2205/3379* (2013.01); *A61M 2230/20* (2013.01)

(56) References Cited

OTHER PUBLICATIONS

Ntziachristos V. et al., "MRI-Guided Diffuse Optical Spectroscopy of Malignant and Benign Breast Lesions", Neoplasia 4(4):347-354 (2002).
Schreiter N.F. et al., "Optical Imaging of Breast Cancer Using Hemodynamic Changes Induced by Valsalva Maneuver", Optical Imaging of . . . Fortschr Rontgenstr 184:358-366 (2012).
Scutt D. et al., Breast Asymmetry and Predisposition to Breast Cancer, Breast Cancer Research 8(2):R14 (7 pages) (2006).
Srinivasan S. et al., "Interpreting Hemoglobin and Water Concentration, Oxygen Saturation, and Scattering Measured In Vivo by Near-Infrared Breast Tomography", PNAS 100(21):12349-12354 (Oct. 14, 2003).
Tromberg B.J. et al., "Non-Invasive In Vivo Characterization of Breast Tumors Using Photon Migration Spectroscopy", Neoplasia 2(1-2):26-40 (Jan.-Apr. 2000).
Nielsen T. et al., "Diffuse Optical Tomography of the Breast: Preliminary Findings of a New Prototype and Comparison With Magnetic Resonance Imaging", Eur Radiol 19:1108-1113 (2009).
Xu R.X. et al., "A Prospective Pilot Clinical Trial Evaluating the Utility of a Dynamic Near-Infrared Imaging Device for Characterizing Suspicious Breast Lesions", Breast Cancer Research 9(6):R88 (12 pages) (2007).
Zhu Q., "Optical Tomography With Ultrasound Localization: Initial Clinical Results and Technical Challenges", Technology in Cancer Research & Treatment 4(3):235-244 (Jun. 2005).
International Search Report dated Aug. 22, 2013 received from Application No. PCT/US2013/038153.

* cited by examiner

SELF-REFERENCING OPTICAL MEASUREMENT FOR BREAST CANCER DETECTION

CROSS-REFERENCE TO RELATED APPLICATIONS

This application claims the benefit of U.S. Provisional Application No. 61/639,132, filed on Apr. 27, 2012.

STATEMENT REGARDING FEDERALLY SPONSORED RESEARCH OR DEVELOPMENT

This invention was made with government support under Contract No. R41CA096102 awarded by the National Institute of Health, and Contact No. DAMD017-03-C-0018 awarded by U.S. Army. The federal government of the United States has certain rights in the invention.

FIELD OF THE INVENTION

The present invention relates to a method for optical measurement for breast cancer detection and an apparatus for effecting the same.

BACKGROUND OF THE INVENTION

Diagnostic imaging methods frequently rely on evidence of anatomical disturbances that confer specific information as to the presence or absence of disease. In the case of functional techniques, such as obtained using magnetic resonance, optical or bioelectric methods, evidence of disease is based on identifying some form of functional disturbance, either under conditions of a resting state or from an evoked response. In the field of neuroimaging, both sets of measures have contributed significantly to our understanding of brain function and of the impact of disease or trauma.

Favoring the use of optical methods for the detection of breast cancer, particularly in the near infrared region, are disturbances originating from tumor angiogenesis, which result in a malformed vascular bed, leading to disturbances in the hemoglobin signal. Knowledge of this has formed the basis of a large number of instrument development and clinical investigations aimed at extracting biomarkers sensitive to these disturbances. Publications that demonstrate such instrument include: B. J. Tromberg, N. Shah, R. Lanning, A. Cerussi, J. Espinoza, T. Pham, L. Svaasand, and J. Butler, "Non-invasive in vivo characterization of breast tumors using photon migration spectroscopy," *Neoplasia* 2, 26-40 (2000); H. Jiang, Y. Xu, N. Iftimia, J. Eggert, K. Klove, L. Baron, and L. Fajardo, "Three-dimensional optical tomographic imaging of breast in a human subject," *IEEE Transactions on Medical Imaging* 20, 1334-1340 (2001); R. Choe, S. D. Konecky, A. Corlu, K. Lee, T. Durduran, D. R. Busch, S. Pathak, B. J. Czerniecki, J. Tchou, D. L. Fraker, A. Demichele, B. Chance, S. R. Arridge, M. Schweiger, J. P. Culver, M. D. Schnall, M. E. Putt, M. A. Rosen, and A. G. Yodh, "Differentiation of benign and malignant breast tumors by in-vivo three-dimensional parallel-plate diffuse optical tomography," *J. Biomedical Optics* 14, 024020 (2009); Q. Fang, S. A. Carp, J. Selb, G. Boverman, Q. Zhang, D. B. Kopans, R. H. Moore, E. L. Miller, D. H. Brooks, and D. A. Boas, "Combined optical imaging and mammography of the healthy breast: optical contrast derived from breast structure and compression," *IEEE Transactions on Medical Imaging* 28, 30-42 (2009); and S. M. van de Ven, S. G. Elias, A. J. Wiethoff, M. van der Voort, T. Nielsen, B. Brendel, C. Bontus, F. Uhlemann, R. Nachabe, R. Harbers, M. van Beek, L. Bakker, M. B. van der Mark, P. Luijten, and W. P. Mali, "Diffuse optical tomography of the breast: preliminary findings of a new prototype and comparison with magnetic resonance imaging," *European Radiology* 19, 1108-1113 (2009). Commonly considered are measures that determine the content of hemoglobin as well as other constituents (e.g., tissue water or lipid content). Discussion on this subject can be found in, for example, S. Srinivasan, B. W. Pogue, S. Jiang, H. Dehghani, C. Kogel, S. Soho, J. J. Gibson, T. D. Tosteson, S. P. Poplack, and K. D. Paulsen, "Interpreting hemoglobin and water concentration, oxygen saturation, and scattering measured in vivo by near-infrared breast tomography," *Proc. National Academy of Sciences USA* 100, 12349-12354 (2003) and S. Srinivasan, B. W. Pogue, S. Jiang, H. Dehghani, C. Kogel, S. Soho, J. J. Gibson, T. D. Tosteson, S. P. Poplack, and K. D. Paulsen, "In vivo hemoglobin and water concentrations, oxygen saturation, and scattering estimates from near-infrared breast tomography using spectral reconstruction," *Academic Radiology* 13, 195-202 (2006). These measures are typically performed without regard to any temporal behavior associated with the hemoglobin signal that may be observable (e.g., presence of natural vascular rhythms).

An alternative approach is to perform optical studies for the purpose of exploring the temporal dynamics of the hemoglobin signal. Prior publications that describe this approach include, for example, P. Schneider, S. Piper, C. H. Schmitz, N. F. Schreiter, N. Volkwein, L. Lüdemann, U. Malzahn, A. Poellinger, "Fast 3D near-infrared breast imaging using indocyanine green for detection and characterization of breast lesions," *Fortschritte auf dem Gebiet der Röntgenstrahlen und der bildgebenden Verfahren* 183, 956-963 (2011); N. F. Schreiter, N. Volkwein, P. Schneider, M. H. Maurer, S. Piper, C. H. Schmitz, and A. Poellinger, "Optical imaging of breast cancer using hemodynamic changes induced by Valsalva maneuver," *Fortschritte auf dem Gebiet der Rontgenstrahlen und der bildgebenden Verfahren* 184, 358-366 (2013). Indeed, consideration of such measures forms the basis of the method of pulse oximetry. While both static and dynamic optical measures of the breast have been implemented, there is a host of factors associated with how measures are taken, the natural variability in breast size and composition, and how data are explored, that have confounded efforts to identify useful biomarkers for the presence of breast cancer without the need for prior information. Most desirable would be to implement a simplified sensing and analysis strategy that is mainly robust to the details of these factors, but nevertheless can reliably yield biometrics that serve to detect and locate the presence of cancerous tumors of the breast.

Similar to the experience gained with bioelectric phenomena of tissue, measures of hemodynamics using optical methods can be explored with the goal of identifying phenomena that either are or are not directly observable. Non-observable phenomena often are the domain of inverse solvers used to derive spatial maps of background tissue coefficients. In the case of bioelectric studies, such efforts are often directed at identifying loci of aberrant neural activity such as those associated with epileptic lesions. Corresponding efforts applied to optical studies of tissue typically seek to generate spatial maps of the background optical absorption and scattering coefficients, from which can be further derived maps of components of the hemoglobin signal, other naturally occurring constituents (i.e., water, lipid content) and features associated with light scattering phenomena. R. Choe et al. (See above); Q. Fang et al. (See above), works of S. Srinivasan et al. (See above), and J. Wang, B. W. Pogue, S. Jiang, and K. D. Paulsen, "Near-infrared tomography of breast cancer hemoglobin, water, lipid, and scattering using combined frequency domain and cw measurement," *Optics Letters* 35, 82-84 (2010) describe this approach.

Experience in other fields has shown that problems of this type, generally referred to as boundary value problems, can be notoriously difficult solve in any stable way. Should the goal be to derive biometrics based on absolute values of tissue constituents, then much detail regarding the particulars of the boundary conditions is required. For an appendage such as the breast, the natural variance in size, internal composition, and deformability make efforts to reliably define the boundary conditions needed to yield stable inverse solutions especially difficult.

In part because of these difficulties, efforts to apply such methods to extract biomarkers have been limited to measures of the hemoglobin signal that are time-independent. Even among these, the natural variance in breast size and composition has made rigorous efforts to apply use of recursive solvers mainly infeasible. As a consequence, efforts to employ inverse solvers frequently adopt use of simplifying methods, some of which are described in S. B. Colak, M. B. van der Mark, G. W. Hooft, J. H. Hoogenraad, E. S. van der Linden, and F. A. Kuijpers, "Clinical optical tomography and NIR spectroscopy for breast cancer detection," *IEEE J. Quantum Electronics* 51, 1143-1158 (1999); J. P. Culver, R. Choe, M. J. Holboke, L. Zubkov, T. Durduran, A. Slemp, V. Ntziachristos, B. Chance, and A. G. Yodh, "Three-dimensional diffuse optical tomography in the parallel plane transmission geometry: evaluation of a hybrid frequency domain/continuous wave clinical system for breast imaging," *Medical Physics* 30, 235-247 (2003); and H. Dehghani, M. M. Doyley, B. W. Pogue, S. Jiang, J. Geng, and K. D. Paulsen, "Breast deformation modelling for image reconstruction in near infrared optical tomography," *Physics in Medicine and Biology* 49, 1131-1145 (2004). A common approach has been to use prior knowledge of reference, unaffected tissue to a region under analysis for which, frequently, the latter is strongly suspected to have cancer. Methods of using prior knowledge for this purpose is described, for example, in N. F. Schreiter et al. (See above); V. Ntziachristos, A. G. Yodh, M. D. Schnall, and B. Chance, "MRI-guided diffuse optical spectroscopy of malignant and benign breast lesions," *Neoplasia* 4, 347-354 (2002); A. Li, E. L. Miller, M. E. Kilmer, T. J. Brukilacchio, T. Chaves, J. Stott, Q. Zhang, T. Wu, M. Chorlton, R. H. Moore, D. B. Kopans, and D. A. Boas, "Tomographic optical breast imaging guided by three-dimensional mammography," *Applied Optics* 42, 5181-5190 (2003); Q. Zhu, "Optical tomography with ultrasound localization: initial clinical results and technical challenges," *Technology in Cancer Research & Treatment* 4, 235-244 (2005); R. X. Xu, D. C. Young, J. J. Mao, and S. P. Povoski, "A prospective pilot clinical trial evaluating the utility of a dynamic near-infrared imaging device for characterizing suspicious breast lesions," *Breast Cancer Research* 9, R88 (2007); and C. M. Carpenter, R. Rakow-Penner, S. Jiang, B. L. Daniel, B. W. Pogue, G. H. Glover, and K. D. Paulsen, "Inspired gas-induced vascular change in tumors with magnetic-resonance-guided near-infrared imaging: human breast pilot study," *J Biomedical Optics* 15, 036026 (2010). While use of such methods does enhance the capability of distinguishing tumors from unaffected tissue, it also reduces their potential practical utility, especially if the goal is to derive biometrics that can serve as a primary screening tool.

An alternative approach to static measures is to explore the naturally occurring dynamics associated with the hemoglobin signal. Experience with other forms of dynamic measures (e.g., bioelectric measures of the brain or heart) indicates that there are a host of factors that can influence signal dynamics, thereby confounding interpretation of potential biomarkers. In the case of optical measures of the hemoglobin signal, time-varying changes can be expected from spontaneous or evoked changes in cardiovascular tone due to effects of posture, presence of commonly prevalent morbidities (e.g., atherosclerosis) and other factors, each of which can be further modified by local variations due to vascular autoregulation. Additionally, because these factors are uncorrelated across individuals, it can be expected that the natural variance associated with dynamics of the hemoglobin signal will be large in any group of individuals. Taken together, it can be expected that natural variance associated with optical measures of the breast should be very large indeed. Such excessive variance can be expected to complicate efforts to derive useful biometrics based on dynamic measures of the breast.

Experience with other forms of functional measures of tissue dynamics (e.g., EEG measures) has emphasized the value of implementing some form of a reference measure that serves to limit the impact of various naturally occurring confounding factors. One consideration regarding a reference measure would be to perform a simultaneous bilateral measurement, wherein information obtained from one breast is used as a reference for the other. Simplest would be to perform a time-independent measurement, in which case the influence of the natural vascular rhythms should be minimal. Certainly, simultaneous bilateral breast measures are routinely performed using the MR method. Here too, however, a brief consideration of the expected impact of natural variances in breast size and composition—for instance, it is known that the left breast is typically larger than the right breast; see D. Scutt, G. A. Lancaster, and J. T. Manning, "Breast asymmetry and predisposition to breast cancer," *Breast Cancer Research* 8, R14 (2006).—on optical measures suggest that inter-subject variances could be very large.

Yet other factors affecting optical measures are the fidelity of optode contact. Being highly deformable, the details of contact could be expected to vary considerably across individuals, depending on measurement geometry. Moreover, the details of contact can be expected to vary even in cases of simple geometries such as a planar arrangement, because even small differences in contact pressure can affect the hemoglobin signal. See, for example, S. D. Jiang, B. W. Pogue, and K. D. Paulsen, "In vivo near infrared spectral detection of pressure-induced changes in breast tissue," *Optics Letters* 28, 1212-1214 (2003), and A. L. Darling, P. K. Yalavarthy, M. M. Doyley, H. Dehghani, and B. W. Pogue, "Interstitial fluid pressure in soft tissue as a result of an externally applied contact pressure," *Physics in Medicine and Biology* 52, 4121-4136 (2007). An expected confounding factor here is the natural variance in breast stiffness, which would cause regions near the chest wall to experience greater loads than regions closer to the nipple. Also confounding is the simple recognition that the signal attenuation with the optical technique is approximately a factor of ten per centimeter. Thus even small variations is breast size, contour, internal composition, or fidelity of optode contact can be expected to significantly influence the measured signal.

These considerations demonstrate that there are many naturally occurring factors, and elements of how data are obtained and treated, that can be expected to complicate the fidelity of derived biomarkers for the presence of cancer based on optical measures.

SUMMARY OF THE INVENTION

An objective measurement can be made for the detection of breast cancer with high diagnostic sensitivity and specificity, without relying on prior knowledge of whether cancer is present or which breast is affected. Novel elements of the invention leverage a combination of factors that consider how optical data is obtained from the breast, use of a simultaneous bilateral referencing protocol, and how data are treated. Specific elements disclosed here include the collection of optical array measurements from both breasts simultaneously under various protocols, including resting-state measures and evoked responses. The developed technique employs economical sensing hardware and data collection protocols that are easily implemented without patient discomfort.

To overcome the limitations imposed by the prior art, various constraints are imposed on data collection and analysis that serve to reduce the natural variance associated with optical measures of the breast. The nature of these constraints fall into three broad categories: (1) imposition of substantially symmetric external boundary conditions; (2) collection of simultaneous bilateral dynamic measures; (3) referencing measures of one breast to another. Additionally, these constraints can be applied either to data obtained under resting state conditions or to an evoked response. Results are presented demonstrating that this combination of methods serves to allow for the detection of breast cancer, and for its localization in the affected breast with high reliability, without the need for prior information.

The methods and teachings outlined in here are intended to provide an objective measurement for the detection of breast cancer. The experimental approach taken is motivated by the general understanding that principal elements of the cancer phenotype include a disturbed vascular bed having enhanced angiogenesis. Typically, the hemoglobin signal accompanying this state includes a condition of enhanced hemoglobin content and reduced hemoglobin oxygenation.

Novel elements of the invention described here include the manner in which optical data is obtained from the breast, the type of protocol used to obtain the optical measures, and the approach applied to the resulting data to derive biometrics that when considered individually or in combination can discriminate individuals having breast cancer from those having benign disease or are free from breast pathology.

Specific elements disclosed here include the collection of optical array measurements from both breasts simultaneously and the ability to apply precise articulation to both breasts simultaneously while performing optical measures. Additional novel elements include the application of a defined respiratory gas maneuver and collection of data from a resting baseline.

According to an aspect of the present disclosure, a system for detecting features within a pair of breasts of a patient is provided. The system includes a diffuse optical measurement system including at least one pair of optical sources and a pair of sensing heads configured to fit a pair of breasts and to simultaneously measure optical tomographical data from the pair of breasts while imposing bilaterally symmetric external boundary conditions for optical tomography upon the pair of breasts. The system further includes a computing means for analyzing the simultaneously measured optical tomographical data by running an automated program. The automated program includes steps of: generating a reference data field, as a function of space and measurement time, based on a first subset of the simultaneously measured optical tomographical data on one of the pair of breasts; performing a statistical analysis on a variation, from the reference data field, of a data field including the simultaneously measured tomographical data for another of the pair of breasts; and generating data that is indicative of presence or absence of breast cancer in the another of the pair of breasts based on the statistical analysis.

According to another aspect of the present disclosure, a method of detecting features within a pair of breasts is provided. At least one pair of optical sources and a pair of sensing heads of a diffuse optical measurement system is mounted to fit a pair of breasts of a patient. Optical tomographical data is simultaneously measured from the pair of breasts while imposing bilaterally symmetric external boundary conditions for optical tomography upon the pair of breasts. The simultaneously measured optical tomographical data is analyzed by running an automated program on a computing means. The automated program includes steps of: generating a reference data field, as a function of space and measurement time, based on a first subset of the simultaneously measured optical tomographical data on one of the pair of breasts; performing a statistical analysis on a variation, from the reference data field, of a data field including the simultaneously measured tomographical data for another of the pair of breasts; and generating data that is indicative of presence or absence of breast cancer in the another of the pair of breasts based on the statistical analysis.

DETAILED DESCRIPTION OF THE INVENTION

As stated above, the present invention relates to a method for optical measurement for breast cancer detection and an apparatus for effecting the same. It is noted that proportions of various elements in the accompanying figures are not drawn to scale to enable clear illustration of elements having smaller dimensions relative to other elements having larger dimensions.

Figure 1:
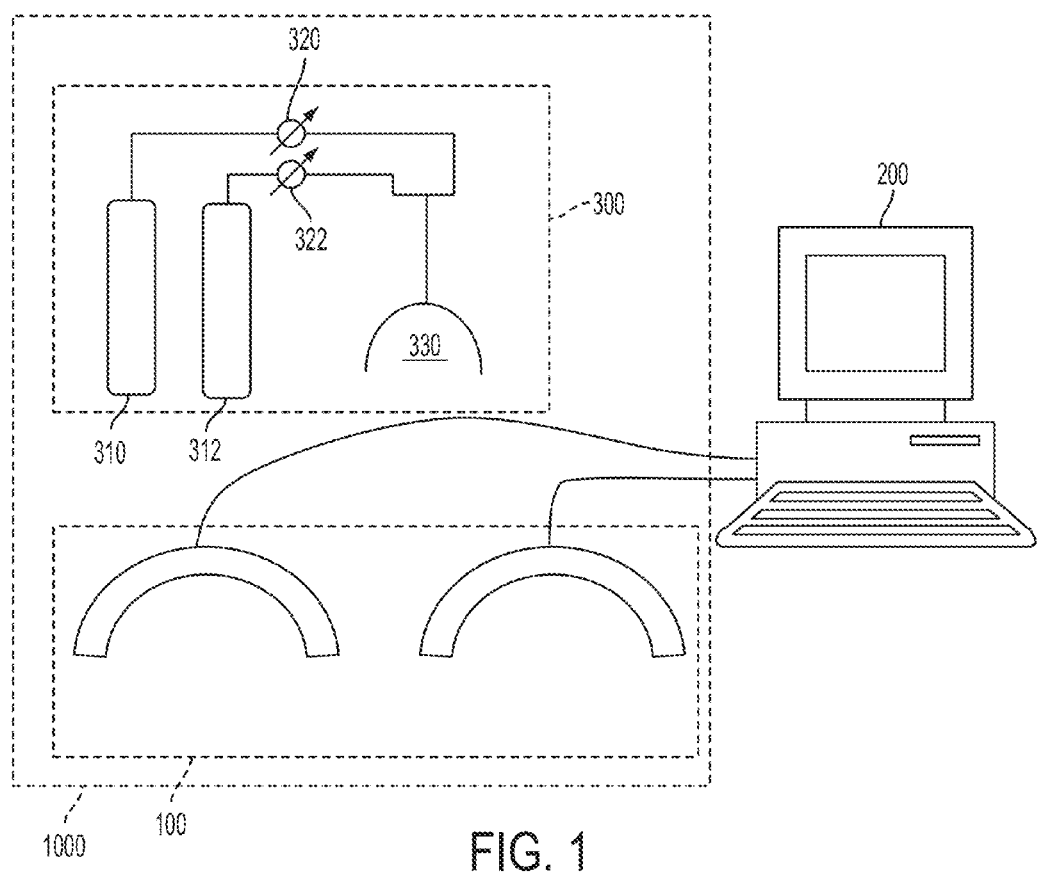
FIG. 1 is a schematic diagram for a system for detecting features in a pair of breasts, according to an embodiment of the present disclosure.

Referring to FIG. 1, an exemplary system for detecting features within a pair of breasts is schematically illustrated. The breasts can be breasts of any mammals and particularly, can be human breasts. As used herein, features within a breast refers to any anomaly within the breast including, but not limited to, cancerous cells, tumors, ruptured breast implants, or any anomalous condition in cells or implanted materials.

The exemplary system includes a diffuse optical measurement system 1000 including a pair of sensing heads 100 configured to fit a pair of breasts (not shown), and to simultaneously measure optical tomographical data from the pair of breasts while imposing bilaterally symmetric external boundary conditions for optical tomography upon the pair of breasts. At least one pair of optical sources can be provided within the pair of sensing heads 100, as separate units that are mounted to the pair of sensing heads 100, or as separate units mounted to the pair of breasts. As used herein, a bilateral symmetry refers to a mirror symmetry about a plane that passes through a spine of a normal vertebrate, or an equivalent plane for a vertebrate having a deformed spine. As used herein, external boundary conditions for optical tomography refers to physical constraints that define volumes to be analyzed by optical tomography. Thus, bilaterally symmetric external boundary conditions for optical tomography upon a pair of breasts provides a pair of mechanical constraints that conform the pair of breasts within a pair of symmetric volumes for performing optical tomography. The at least one pair of optical sources include at least one light source for each of the pair of breasts. The at least one pair of optical sources can include a plurality of light sources controlled by a computing means 200, which can be, for example, a computer that runs an automated program that controls emission and detection of light from the at least one pair of optical sources. The optical sources can be, for example, infrared light sources. Each sensing head includes at least one detector, and can include a plurality of detectors, which transmits the measured data to the computing means 200. The diffuse optical measurement system 1000 can be a diffuse optical tomography system configured to generate two-dimensional or three-dimensional tomographic images, or can be configured to provide a digital output as to the condition of the examined pair of breasts such as "no cancer," "cancer suspected," or "further examination needed."

The exemplary system further includes a computing means 200 for analyzing the simultaneously measured optical tomographical data by running an automated program. The computing means 200 can be a personal computer known in the art, a server, a cloud computing environment as known in the art, and/or a portable computing device provided that the computing means 200 can run the automated program for processing the data from the diffuse optical measurement system 1000.

In one embodiment, the pair of sensing heads 100 can be configured to provide a bilaterally symmetric articulation while measuring the optical tomographical data. During the bilaterally symmetric articulation, the pair of sensing heads 100 maintains the mirror symmetry.

The diffuse optical measurement system 1000 can further includes a means 300 for altering a composition of a respiratory gas supplied to a patient from whom the optical tomographical data is simultaneously measured. The means 300 for altering the composition of the respiratory gas can include, for example, an oxygen supply system 310, an oxygen flow regulator 320, a carbon dioxide supply system 312, a carbon dioxide flow regulator 322, and a gas mask 330 configured to provide the respiratory gas to the patient.

The pair of sensing heads 100 of the diffuse optical measurement system 1000 can be mounted to fit a pair of breasts of the patient. Subsequently, optical tomographical data can be simultaneously measured from the pair of breasts while imposing bilaterally symmetric external boundary conditions for optical tomography upon the pair of breasts. In one embodiment, the simultaneously measured optical tomographical data can include data on hemodynamic response or vascular tone. For example, the simultaneously measured optical tomographical data can include an oxyhemoglobin level and a deoxyhemoglobin level. In one embodiment, the optical tomographical data can be measured under a condition of a resting state. In another embodiment, the optical tomographical data can be measured after inducing an evoked change in cardiovascular tone or cardiovascular functionality of the patient.

Subsequently, the simultaneously measured optical tomographical data can be analyzed by running an automated program on the computing means 200. The automated program can include a step of generating a reference data field, as a function of space and measurement time, based on a first subset of the simultaneously measured optical tomographical data on one of the pair of breasts. Further, the automated program can include a step of performing a statistical analysis on a variation, from the reference data field, of a data field including the simultaneously measured tomographical data for another of the pair of breasts. Yet further, the automated program can include a step of generating data that is indicative of presence or absence of breast cancer in the other of the pair of breasts based on the statistical analysis.

In one embodiment, the variation can be measured for each pair of corresponding physical points that are present in the pair of breasts and are mapped to each other by a mirror symmetry inherent in the bilaterally symmetric external boundary conditions. Further, the statistical analysis includes an outlier analysis that identifies locations of physical points at which an absolute value of the variation is greater than a predefined multiple of a standard deviation of the variation. The range of values for the predefined multiple may be, for example, in a range from 3 to 6, although lesser and greater values can also be employed.

In one embodiment, local averaging of the measured optical tomographical data can be performed for a subset of data generated at the same time with suitable weighting around each point in one of the two breasts. Exclusion of data taken at any different time from the locally averaged data facilitates reduction of time-dependent noise in the locally averaged data. The local averaging can employ a weighting function such as a Gaussian function. The lateral extent of the weighting function, such as the standard deviation of the Gaussian function, can be selected to minimize noise in data while avoiding undue suppression of signal indicative of cancerous growth or other anomalies. For example, the lateral extent of the weighting function can be in a range from 2 mm to 5 cm, although lesser and lateral extents can also be employed. In one embodiment, the locally averaged data includes weighted averages only within a single breast. In another embodiment, the locally averaged data can include weighted averages that are taken across corresponding symmetric regions of the two breasts.

In one embodiment, the generation of the reference data field can be performed by spatially averaging the measured optical tomographical data, or data derived therefrom, across the pair of breasts. In one embodiment, the spatial averaging of the measured optical tomographical data, or of data derived therefrom, can be performed only for synchronous data, while excluding data taken at a different time. Limiting the averaging of the data to spatial averaging and not performing averaging over time can help reduce variables introduced by time-variant variables such as the effect of breathing or the effect of evocation. In one embodiment, the generation of the reference data field as a function of space and measurement time can be performed employing solely the simultaneously measured optical tomographical data, without employing data generated from any other physical breast than the pair of breasts or from any model for a physical breast.

In one embodiment, the reference data field includes at least one of: a total hemoglobin level; a hemoglobin oxygen saturation; and a measure of hemoglobin oxygen extraction efficiency.

Preferred Embodiment

1. Simultaneous Bilateral Breast Measures

Figure 2:
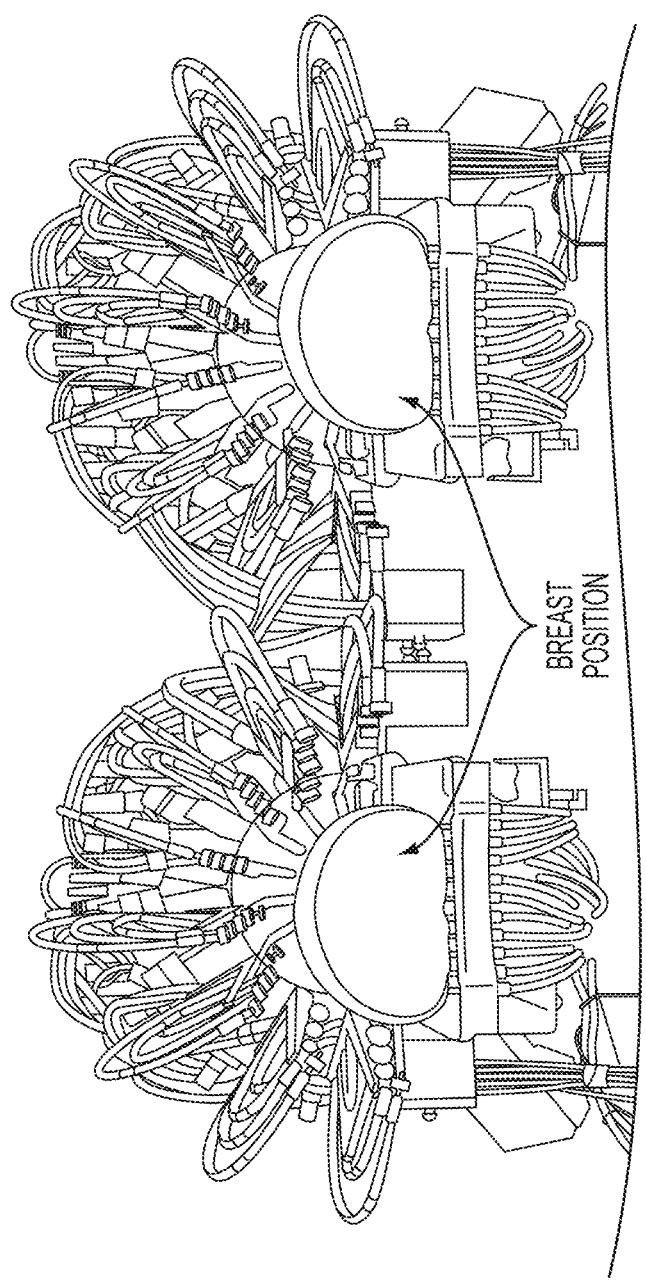
FIG. 2 is a photograph of an articulating dual optical sensing head for simultaneous bilateral breast studies, according to an embodiment of the present disclosure.

Referring to FIG. 2, a dual sensing head apparatus is shown, which has been implemented in an effort to reduce sources of variance inherent to optical measures of the breast. The dual sensing head structure (1) provides for simultaneous bilateral measures, (2) serves to impose substantially bilaterally symmetric external boundary conditions by employing feedback-controlled articulation members that can adjust optode contact force to a desired value. A description of this setup and methods used to evaluate the hemoglobin signal are given in R. Alabdi, H. L. Graber, Y. Xu, and R. L. Barbour, "Optomechanical imaging system for breast cancer detection," *J. Optical Society of America A* 28, 2473-2493 (2011). Briefly, each breast is illuminated in parallel with dense array of sources (760, 830 nm), in rapid succession, with a parallel recording of the emerging light intensity.

It is appreciated by those skilled in the art that there are multiple ways in which optical source and illumination schemes can be adopted to effect an array-type measure. Here, a time-multiplexing scheme applied to steady-state, also known as continuous wave (CW) measurements, has been adopted. Measures in the frequency domain, wherein optical sources are modulated in the radiofrequency range, as well as ultrafast, time-domain measures can also be employed. Further, optical measures can consider either substantially single wavelength sources or multiwavelength sources that emit light over a relatively narrow (e.g., laser diodes) or relatively broad (LEDs) wavelength range. In addition, a range of light detection schemes can be considered. This includes silicon photodiodes, avalanche photodiodes, photomultiplier tubes, streak cameras, and CCD cameras, among others. Among the various considered sensing approaches, these can be accomplished with or without intervening optical fibers.

The array-type measure employed here produces a large number of detector time-series recordings (2048/breast/wavelength), from which a 4D image time series of various components of the hemoglobin signal can be computed, using methods known in the art. The particular setup shown in FIG. 2 also allows for the introduction of precisely controlled articulation maneuvers similar in spirit to the tactile sensing accomplished by a physician during a clinical breast exam. Here, one aim is to record the hemodynamic response from the breast to a precisely controlled, event-related articulation. In cases where the aim is restricted to recording the hemodynamic response of the breast without articulation, a notably more simple sensing arrangement can be adopted. One such example that still achieves the aim of imposing substantially bilaterally symmetric external boundary conditions is the use of a typical brassiere in which are embedded the sensing elements. Both types of arrangement. however. are suitable for recording resting-state responses as well as event-related responses. A simple example of the latter includes having subjects inhale different mixtures of respiratory gases.

As noted above, independent of what type of measure is performed (i.e., resting state, evoked response), a confounding factor that has thus far limited the utility of optical measures of the breast has been the multitude of sources of variance inherent to these measures. Methods are demonstrated below that demonstrate that the combination of constraints outlined above can serve to significantly improve the delectability of breast cancer based on time-varying optical measures.

In one embodiment, the articulating elements that house optical fibers and that serve to deliver light to and receive reemitted light from the breast are adjusted under feedback control to achieved a specified contact force (typically, 1.8 N) with the breast surface within a dual sensing-head structure such as the one illustrated in FIG. 2. Having successfully positioned the breasts within the sensing heads and achieved the desired contact force, a resting baseline measure is made lasting approximately five minutes, during which time the subject is resting comfortably in the seated position. During this time, optical measures involving the complete array of optical source positions and detector positions are obtained using a time-multiplexing scheme. In the considered example here (see section below labeled "Clinical Study"), the measurement involved 64 detector positions and 32 source positions for each breast. Additionally, the frequency of data sampling using a dual-wavelength optical source (760 nm and 830 nm) across the complete array was approximately 2 Hz. This sampling rate is equivalent to performing more than 8000 optical measures for each complete cycle of the sensing array.

Following this, the articulating elements within the sensing head are adjusted to achieve a desired applied force. Because each articulating element is controlled separately, the sequence, time duration and magnitude of applied force can be varied to achieve a desired response. In the considered case explored here (see Clinical Study, below), articulation was achieved by adjusting the two elements located within the most medial and most lateral aspects of each sensing head (i.e., total of four elements employed per sensing head) to achieve a target applied force of 7.1 N.

Other combinations of the articulating elements can also be considered. For the particular example considered here, during articulation, the position of the remaining elements was held fixed at a predetermined contract force (e.g., 1.8 N). The resulting identified maneuver accomplishes a simultaneous medial-lateral compression of each breast. Having achieved the desired articulation movement for the selected articulating elements, a time-series optical measurement is again obtained from both breasts simultaneously.

Figure 3:
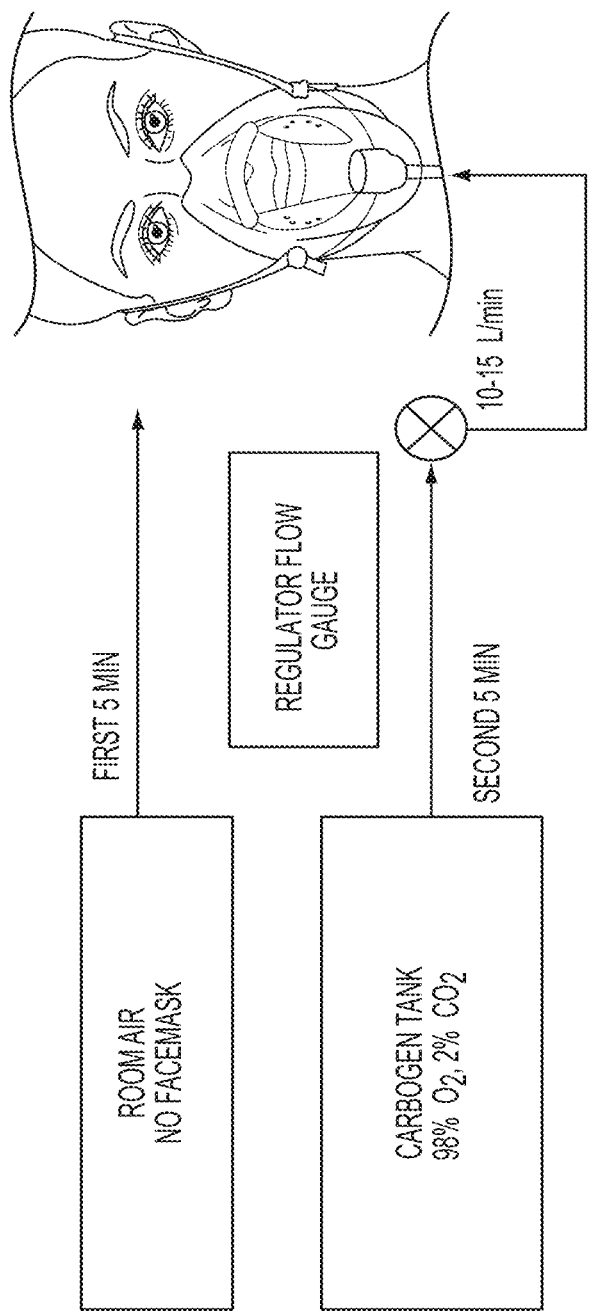
FIG. 3 shows an exemplary experimental setup for adjustment of respiratory gases.

Following this a third experimental measurement is obtain by adjustment of the inhaled respiratory gases. FIG. 3 shows an exemplary experimental setup used to adjust the respiratory gas given to a subject. A carbogen mixture consisting of 98% oxygen and 2% $CO_2$ has been used. Other mixtures such as 95% oxygen and 5% $CO_2$, 100% oxygen only and room air with 5% $CO_2$ could also be used, as well as other gas mixtures. The purpose of employing the respiratory gas is to evoke a change in the hemoglobin signal, either by adjusting the partial pressure of oxygen in the blood and/or by evoking a vascular response that affects vasotone (e.g., as caused by elevated levels of oxygen to increase hemoglobin oxygen saturation and induce partial vasoconstriction, and/or by introducing elevated levels of $CO_2$ as a means to induce vasodilatation). Gas delivery can be achieved using masks that partially or completely exclude rebreathing of expired air from the lungs. Additionally, accompanying gas delivery can be independent measures of gas composition to ensure fidelity of mask-face contact.

The sequence of data collection (i.e., baseline, articulation, respiratory gas adjustment) can be changed to include other combinations of the protocol (e.g., baseline, respiratory gas adjustment, articulation).

Having obtained the indicated optical measures using the protocols identified above, the optical data for each source-detector pair is transformed using a modified Beer-Lambert law as described by, for example, C. H. Schmitz, D. P. Klemer, R. E. Hardin, M. S. Katz, Y. Pei, H. L. Graber, M. B. Levin, R. D. Levina, N. A. Franco, W. B. Solomon, and R. L. Barbour, "Design and implementation of dynamic near-infrared optical tomographic imaging instrumentation for simultaneous dual-breast measurements," *Applied Optics* 44, 2140-2153 (2005). This data can be subsequently transformed using additional methods to achieve a desired result (e.g., 3D image reconstruction as described by Y. Pei, H. L. Graber, and R. L. Barbour, "Influence of systematic errors in reference states on image quality and on stability of derived information for DC optical imaging," *Applied Optics* 40, 5755-5769 (2001)). Specific examples as to how the collected data can be processed are described subsequently.

1.1 Baseline Measures:

In the case of the baseline measures, the desired result is to compute a measure of central tendency obtained from the collected optical time series data. This can include measures of the hemoglobin signal computed before or after 3D image reconstruction. Because an array of sensor data is collected over a specified time period, measures of central tendency comprise information obtained from both the temporal and spatial domains.

For instance, in the considered example the data transformation steps were as follows:

Step 1: Normalize optical measures obtained from each source-detector pair and optical wavelength for each breast to its respective temporal mean value obtained over the baseline period. The resulting measures can be thresholded using a defined criterion (e.g., temporal variance) to exclude excessively noisy channels.

Step 2: Transform the normalized dual-wavelength sensor data from Step 1 to yield 3D images of the hemoglobin signal of the breast at each time point. Elements of the computed hemoglobin signal can include individual (i.e., oxyhemoglobin, deoxyhemoglobin) or composite measures (e.g., hemoglobin oxygen saturation, total hemoglobin (algebraic sum of oxyhemoglobin and deoxyhemoglobin), oxygen extraction efficiency (deoxyhemoglobin minus oxyhemoglobin), or other combinations as discussed in G. W. Wylie, H. L. Graber, G. T. Voelbel, A. D. Kohl, J. DeLuca, Y. Pei, Y. Xu, and R. L. Barbour, "Using co-variations in the Hb signal to detect visual activation: A near infrared spectroscopic imaging study," *NeuroImage* 47, 473-481 (2009)).

Step 3: Having computed the image time series from Step 2, the resulting 4-dimensional data set is reduced, first by computing the spatial standard deviation (variance) (SSD) from each 3D image in the image time series and next by computing the temporal mean TM of the resulting one-dimensional time series. For brevity, this quantity is referred to as TMSSD. The substantially equivalent measures can be derived by rearranging the order in which the dimensionality reduction is achieved. For instance, the temporal standard deviation of each image pixel time series could be first computed to yield a single 3D image of the temporal variance. The resulting spatial map could be further reduced to a scalar quantity by computing the spatial variance of this map (i.e., spatial standard deviation of the temporal mean, SSDTM). Alternatively, the equivalent operations could be applied to the sensor array data without the need to implement 3D image reconstruction. Regardless, the resulting scalar quantity is sensitive to spatial variations in the hemoglobin signal, as can be produced by a cancerous tumor, whose average amplitude can be determined by computing its temporal mean (variance) value.

Step 4: Having obtained results from Step 3 for each breast, in one embodiment, a paired difference value can be computed by subtracting the derived quantity obtained for one breast from the derived quantity for the other breast, i.e., by computing a difference between corresponding points related by the mirror symmetry. Because breast cancer can occur in either breast, the order of the subtraction is adjusted (and kept track of) to yield a positive value. In another embodiment, a paired ratio value can be computed by dividing the derived quantity obtained for one breast by the derived quantity for the other breast. Because breast cancer can occur in either breast, the order of the division is adjusted (and kept track of) to yield a value greater than unity.

The considered steps can be used to derive equivalent quantities for each element of the hemoglobin signal or combination thereof. An equivalent series of steps can be applied directly to the sensing array data without performing an image reconstruction computation.

1.2 Articulation Maneuver:

Optical measures obtained during periods of defined articulation are processed as follows:

Step 1: Implement defined articulation maneuver while obtaining simultaneous bilateral time-series optical measures from each breast.

Step 2: Apply Step 1 outlined in Baseline Measures to collected data obtained during the period of applied articulation.

Step 3: Using the normalized time series measures obtained from Step 2, compute the associated values of the hemoglobin signal for each source-detector pair comprising the sensing array for each breast.

Step 4: Using the normalized hemoglobin time series obtained from Step 3, compute the spatial variance (standard deviation) across the sensor array for each breast, thereby producing a one-dimensional time series for each breast.

Step 5: Using the time series obtained from Step 4, compute a paired difference value by subtracting the derived quantity obtained for one breast from the derived quantity obtained for the other breast, at a selected time point or over a specified time interval following completion of the specified articulation maneuver. In another embodiment, Step 3 through 5 can include transformation of source-detector pair data to form a 4D image time-series of the breast using methods discussed in Y. Pei, H. L. Graber, and R. L. Barbour, "Influence of systematic errors in reference states on image quality and on stability of derived information for DC optical imaging," *Applied Optics* 40, 5755-5769 (2001).

In practice, the time required to advance from a baseline applied force value to a final articulation force value is less than three seconds. Having achieved this final value, this condition is maintained for a period lasting on the order of 1 minute. Longer or shorter time intervals could also be considered. Note that the steps involved in processing data acquired from the articulation maneuvers do not necessarily require computing an image time series. Additionally, the specific scalar quantity reduced from the original data need not be limited to elements of only the spatial domain. Similar to consideration of baseline data, dimensionality reduction across both domains (time and space) can be considered (e.g., TMSSD, SSDTM).

1.3 Respiratory Gas Maneuvers:

Implement a defined respiratory gas maneuver that involves switching from breathing of room air to a defined gas mixture (See FIG. 3). Having achieved a quasi steady-state condition, optical measures obtained simultaneously from both breasts during periods of respiratory gas maneuvers are processed as follows:

Step 1: Apply Steps 1 and 2 as outlined in Baseline Measures to collected data obtained during the period of applied gas maneuver, to yield a 4D image time series of the hemoglobin signal for each breast.

Step 2: Using images obtained from Step 1, compute a difference map for each breast for individual or combined elements of the hemoglobin signal, by subtracting the value obtained for a selected time instant or time interval during the baseline period from an equivalent value obtained following having achieved a quasi steady-state during the period of the respiratory gas maneuver.

Step 3: Using the difference image obtained from Step 2 for each breast, select a region of interest (ROI) within the image map for subsequent data processing. The considered ROI could include the entire image volume or a subset of the image volume.

Step 4: Compute a measure of central tendency (e.g., spatial mean, spatial variance) from the selected ROI obtained from Step 4.

Step 5: Using the measure of central tendency obtained from Step 4, compute a paired difference value by subtracting the derived quantity obtained from the selected ROI for one breast from the derived quantity obtained from the corresponding region of the other breast.

For each of the indicated derived values, the specific biometric can be obtained for specified elements of the hemoglobin signal, or combinations thereof, involving either all elements of the sensing array or subsets as suggested by the report by Al abdi et al.

EXAMPLES

Example 1: Detection of Breast Cancer from Resting-State Measures

In general, the resting state dynamics of the hemoglobin signal in any tissue are affected by local metabolic and systemic control mechanisms. For many forms of cancer, it is also appreciated that up-regulation of enzyme pathways accompanies the various changes in gene expression. One pathway in particular that is frequently up-regulated is that involving the inducible form of nitric oxide synthase, also known as NOS II. Among its many actions, nitric oxide (NO) is a powerful vasodilator. Previous reports in the literature have identified that subjects with breast cancer experience enhanced modulation of the spontaneous low-frequency vascular rhythms, and that this behavior is sensitive to inhibitors of NOS II. See, for example, T. M. Button, H. Li, P. Fisher, R. Rosenblatt, K. Dulaimy, S. Li, B. O'Hea, M. Salvitti, V. Geronimo, C. Geronimo, S. Jambawalikar, P. Carvelli, and R. Weiss, "Dynamic infrared imaging for the detection of malignancy," *Physics in Medicine and Biology* 49, 3105-3116 (2004).

Here, a group-level study has been performed, which has explored the diagnostic potential of various biomarkers derived from measures of this behavior.

A result produced by performing a simultaneous bilateral optical measure under resting state conditions is a time series from a large number of sensors (2048/breast). As with other forms of time-varying signals (e.g., EEG), this data can be treated in any of a number of ways to extract directly observable or non-observable information. One approach of particular interest is to transform the surface measures to yield a 4D image time series that corresponds to different components of the hemoglobin signal. This includes two measured quantities, oxyhemoglobin (oxyHb) and deoxyhemoglobin (deoxyHb), and up to three derived quantities, total hemoglobin (oxyHb+deoxyHb=totalHb), hemoglobin oxygen saturation ([oxyHb/totalHb]×100=Hbsat), and a measure of hemoglobin oxygen extraction efficiency (doxyHb−oxyHb=Hbext). Having performed such transformations, one is still left with a large amount of data, all of which is sensitive to the concerns raised above as discussed above.

In an effort to reduce sources of variance, one previously identified approach is to employ a normalization scheme that serves to greatly reduce the influence that incomplete knowledge of boundary conditions have on computed coefficient values. While this technique preserves temporal behavior information with good fidelity, the employed normalization necessarily loses information concerning absolute background coefficient values (R. Alabdi, H. L. Graber, Y. Xu, and R. L. Barbour, "Optomechanical imaging system for breast cancer detection,"*J. Optical Society of America A* 28, 2473-2493 (2011)). Because tumor angiogenesis is known to affect these levels, loss of this information potentially can significantly reduce the resulting information value of derived biometrics. In the limit, two breasts having the same temporal response but different background coefficients (e.g., elevated levels of deoxyHb in the affected breast) will appear indistinguishable.

Apart from this loss of information, a simple visual inspection of a 4D image time series is generally uninformative. It is therefore necessary is to employ a data reduction method that can preserve critical information specific to altered functionality caused by a tumor.

One consideration is to extract measures of central tendency applied to the image time series. It may be apparent to those skilled in the art that, because of the nonlinear operation performed by a computation of variance, the order of operations used to compute these measures will affect the computed value. Thus, the value of the spatial mean of the temporal standard deviation is generally not equal to the value of temporal standard deviation of the spatial mean. Application of these transformations reduces a 4D time series to single scalar quantities, of which there are five unique quantities obtainable from measures of the various components of the Hb signal: the spatial mean of the temporal standard deviation (SMTSD), spatial standard deviation of the temporal standard deviation (SSDTSD), temporal mean of the spatial standard deviation (TMSSD), temporal standard deviation of the spatial mean (TSDSM), and temporal standard deviation of the spatial standard deviation (TSDSSD). To a first consideration, these quantities potentially can serve as biomarkers for the presence of cancer.

A simple examination of group-level data would be to compare measures of central tendency (mean, variance) from women with cancer to the same measures from those without. Note that here the lateral information (e.g., left breast in affected group compared to left breast in unaffected group) has been employed, thereby avoiding the expected additional variance due to the natural laterality differences in breast size.

Data listed in Tables 1 and 2 was obtained from age-matched women with tumors in the left or right breast, respectively. There were 45 subjects in the unaffected group (women having no known breast pathology (N=22) and women with various benign pathologies (N=23)), and 12 and 6 subjects with left- and right-breast cancerous tumors, respectively, in the affected group. Inspection of these results shows that despite use of such prior knowledge, none of the measured quantities show group-level differences.

TABLE 1

Student's t-test findings for unilateral comparisons

| Hb Signal Component | Evaluation Approach | Left-Breast Tumor | | | | |
| --- | --- | --- | --- | --- | --- | --- |
| | | SMTSD | SSDTSD | TMSSD | TSDSSD | TSDSM |
| oxyHb | Unilateral | 0.64 | 0.99 | 0.67 | 0.63 | 0.099 |
| deoxyHb | Unilateral | 0.12 | 0.21 | 0.15 | 0.62 | 0.69 |
| totalHb | Unilateral | 0.81 | 0.42 | 0.67 | 0.73 | 0.093 |
| Hbsat | Unilateral | 0.11 | 0.17 | 0.14 | 0.43 | 0.27 |
| Hbext | Unilateral | 0.17 | 0.26 | 0.20 | 0.70 | 0.88 |

TABLE 2

Student's t-test findings for unilateral comparisons

| Hb Signal Component | Evaluation Approach | Right-Breast Tumor | | | | |
| --- | --- | --- | --- | --- | --- | --- |
| | | SMTSD | SSDTSD | TMSSD | TSDSSD | TSDSM |
| oxyHb | Unilateral | 0.21 | 0.25 | 0.20 | 0.51 | 0.86 |
| deoxyHb | Unilateral | 0.13 | 0.14 | 0.13 | 0.52 | 0.20 |
| totalHb | Unilateral | 0.38 | 0.48 | 0.39 | 0.52 | 0.98 |
| Hbsat | Unilateral | 0.10 | 0.11 | 0.11 | 0.41 | 0.085 |
| Hbext | Unilateral | 0.12 | 0.13 | 0.12 | 0.49 | 0.26 |

TABLE 3

Student's t-test findings for bilateral comparisons

| Hb Signal Component | Evaluation Approach | Left-Breast Tumor | | | | |
| --- | --- | --- | --- | --- | --- | --- |
| | | SMTSD | SSDTSD | TMSSD | TSDSSD | TSDSM |
| oxyHb | Bilateral | 0.0057 | 0.0078 | 0.0058 | 0.12 | 0.031 |
| deoxyHb | Bilateral | 0.0022 | 0.0016 | 0.0019 | 0.0038 | 0.013 |
| totalHb | Bilateral | 0.0067 | 0.014 | 0.0089 | 0.29 | 0.037 |
| Hbsat | Bilateral | 0.0025 | 0.0017 | 0.0020 | 0.0013 | 0.0075 |
| Hbext | Bilateral | 0.0044 | 0.0034 | 0.0036 | 0.0023 | 0.027 |

TABLE 4

Student's t-test findings for bilateral comparisons

| Hb Signal Component | Evaluation Approach | Right-Breast Tumor | | | | |
|---|---|---|---|---|---|---|
| | | SMTSD | SSDTSD | TMSSD | TSDSSD | TSDSM |
| oxyHb | Bilateral | 0.0033 | 0.0067 | 0.0046 | 0.022 | 0.052 |
| deoxyHb | Bilateral | 0.0011 | 0.0024 | 0.0016 | 0.0098 | 0.015 |
| totalHb | Bilateral | 0.0044 | 0.011 | 0.0072 | 0.096 | 0.047 |
| Hbsat | Bilateral | 0.00071 | 0.0014 | 0.0010 | 0.0037 | 0.0056 |
| Hbext | Bilateral | 0.0015 | 0.0025 | 0.0017 | 0.0072 | 0.056 |

However, the availability of a simultaneous bilateral measure supports examination of the inter-breast response. One treatment of the data is to compute the ratio of value of the various metrics (left breast/right breast) for the different components of the Hb signal. In contrast to the findings in Tables 1 and 2, this transformation of the data, shown in Tables 3 and 4, indicates that nearly all of the various measures of central tendency are now highly significantly different between the two groups. Note that unlike previous investigations that have adopted optical methods to detect breast cancer, here specific information as to the presence of cancer was not used to affect how a metric value was computed.

Figure 4:
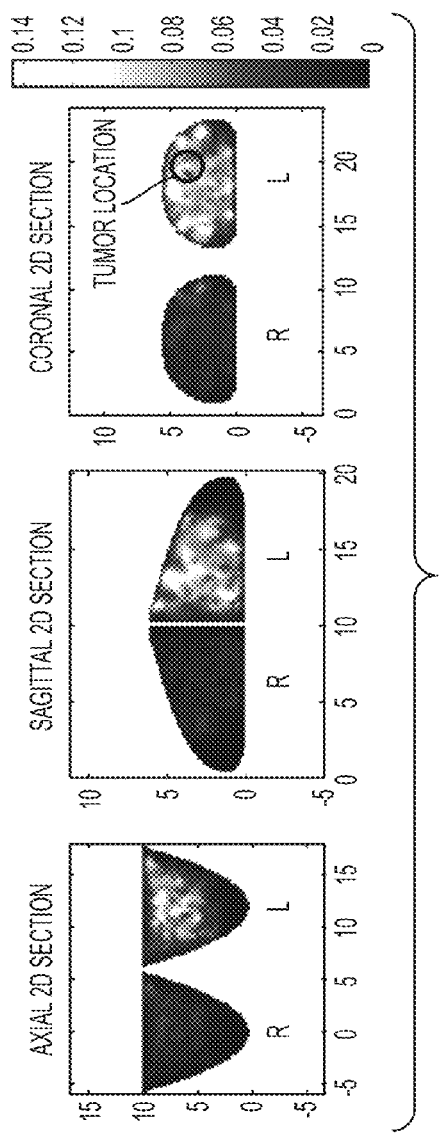
FIG. 4 shows transects through the computed volumetric image for one subject having a tumor (4 cm diameter) in the left breast, along with the equivalent information obtained from the unaffected contralateral breast.
Figure 5:
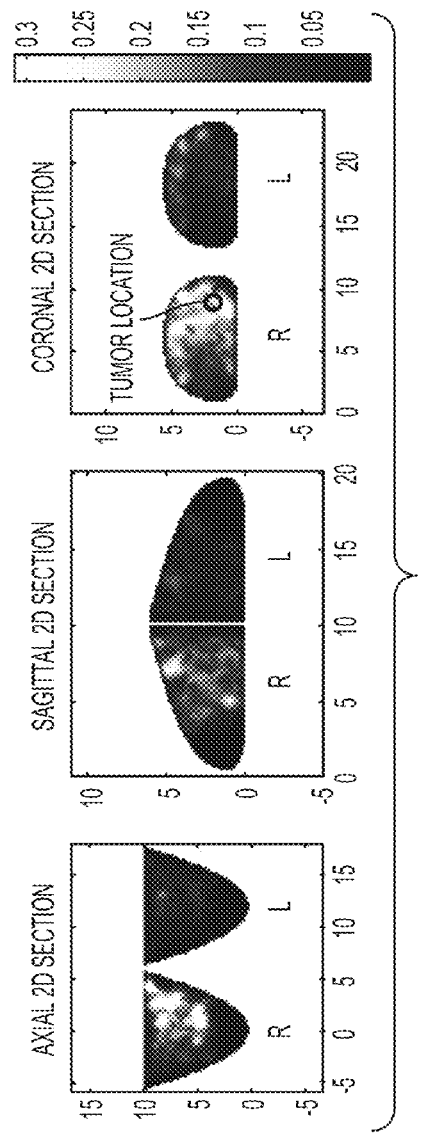
FIG. 5 shows transects through the computed volumetric image for one subject having a tumor (1 cm diameter) in the right breast, along with the equivalent information obtained from the unaffected contralateral breast.

The origin of this discriminatory response can be appreciated by examining a spatial map of the temporal standard deviation of the resting-state behavior obtained from the computed 4D image results. Shown in FIGS. 4 and 5 are transects through the spatial maps of computed temporal standard deviation (TSD), for two subjects having tumors in the left (4 cm diameter) and right (1 cm diameter) breasts, respectively, along with the equivalent information obtained from the unaffected contralateral breast. Inspection reveals that the amplitude of the TSD contrast feature is notably increased in the affected breast, and that it is diffusely dispersed. Interestingly, the spatial extent of the enhanced contrast appears mainly uncorrelated with the tumor's position or its size. This finding is consistent with the expectation of enhanced production of nitric oxide (NO) commonly associated with tumor formation. Being a highly diffusible gas, NO can permeate well beyond the tumor border. Representing a surrogate marker for the actions of NO, optical sensitivity to this factor arises from its effect on the surrounding vasculature. Thus, whereas the considered elements of tumor biology are generally appreciated, not evident is a measurement and analysis methodology that can support extraction of biometrics whose information content does not require use of prior knowledge to derive the considered metric. Also not evident is the consideration that adoption of a normalization scheme that obscures background contrast features should nevertheless be capable of isolating tumor features in a sufficiently stable way to support detection of tumors without use of prior knowledge, when used in combination of other techniques identified herein.

Results from a receiver operator characteristic (ROC) analysis applied to selected portions of this data are shown in Table 5, indicating that the diagnostic sensitivity and specificity of the method without the need for prior knowledge is between 83%-91%, depending on metric. Conditions employed to generate these findings include the establishment of a substantially symmetric external boundary condition between the two breasts (equal contact pressure for each articulating element was applied), adoption of a bilateral referencing scheme, and simultaneous bilateral measures. Its worth noting that the finding a diffuse response to the temporal contrast features seen under resting state conditions strongly suggests that use of a more simplified sensing arrangement, such as could be accomplished using a brassiere embedded with sensing elements, could effect an equivalent measurement.

Table 5 lists the diagnostic accuracy parameters obtained from an ROC analysis computation. NCa and NNon-Ca refer to the numbers of subjects who do and do not have breast cancer, respectively. AUC refers to "area under (the) curve," which is an index of overall diagnostic accuracy. Sens. (%) and Spec. (%) refer to the sensitivity and specificity, respectively, of the metrics indicated in the first column to the presence of breast cancer. (For all three of AUC, Sens. and Spec., the range of possible values is 0%-100% and larger is better.) #FPs and #FNs refer to the absolute numbers of false positive and false negative classifications, respectively.

TABLE 5

Student's t-test findings for bilateral comparisons

| Metric SMTSD | Hb Signal Component | Left-Breast Tumors, $N_{Ca} = 12$, $N_{Non-Ca} = 45$ | | | | |
|---|---|---|---|---|---|---|
| | | AUC (%) | Sens. (%) | Spec. (%) | # FPs | # FNs |
| SMTSD | HbSat | 84.8 | 83.3 | 88.9 | 5 | 2 |
| SSDTSD | HbSat | 85.7 | 83.3 | 91.1 | 4 | 2 |
| TMSSD | HbSat | 85.4 | 83.3 | 88.9 | 5 | 2 |

Example 2: Detection of Breast Cancer from an Evoked Response

To those skilled in the art, it can be appreciated that whereas there are many forms of evoked response that could be considered that may reveal, in some instances, some type of differential response in a breast containing a tumor (e.g., use of various respiratory gas mixtures, applied force maneuvers, Valsalva maneuver) all of the concerns identified above would still apply to the expected impact that the many sources of variance would have on the stability of derived biometrics. For instance, a simple maneuver easily implemented is an applied force to achieve some level of breast compression. A brief consideration, however, indicates that the response one might observe could be highly idiosyncratic and strongly dependent on a host of external boundary and internal constituent factors (e.g., breast stiffness). In the case where the goal is to extract non-observable features (e.g., a tomographic imaging study), the obvious change in breast shape, and hence optical pathlength, would significant affect efforts to recover coefficient values without careful attention to modeling parameters (e.g., details of external boundary, optode position, internal composition). One mitigating approach that might be considered would be to employ the normalization scheme mentioned above, as this has been shown relatively insensitive to image distortions caused by incomplete knowledge of the external boundary. Even here, however, as reported in R. Al abdi et al., the details of the image response are highly dependent on whether or not analyzed data include optical transmission measures (cf. FIGS. 11 and 13 in R. Al abdi et al). Despite these concerns, because there are several notable functional differences between healthy and tumor tissue (e.g., enhanced angiogenesis, increased stiffness), it would nevertheless have significant value to identify a general strategy that might make use of responses from evoked maneuvers in a manner that minimizes inter-subject variances.

Following the thought process outlined above, a simple consideration would be to compare image findings seen in the breast of an affected subject to equivalent findings from an unaffected group. In the case of a compression maneuver, the obvious gross differences in breast sizes among individuals, and the fact that optical energy is exponentially attenuated, makes it remote that consistent differences could be identified that would serve to identify affected individuals. Another consideration might be to implement some form on referencing scheme. One approach previously considered would be to compare regions of unaffected tissue to the affected regions. While this can be effective, as noted, use of such prior knowledge restricts the practical utility of such measures to, at best, a confirmatory method. As with the considerations identified above for resting-state measures, best would be to identify biometrics whose computation does not require specific prior knowledge.

Figure 6:
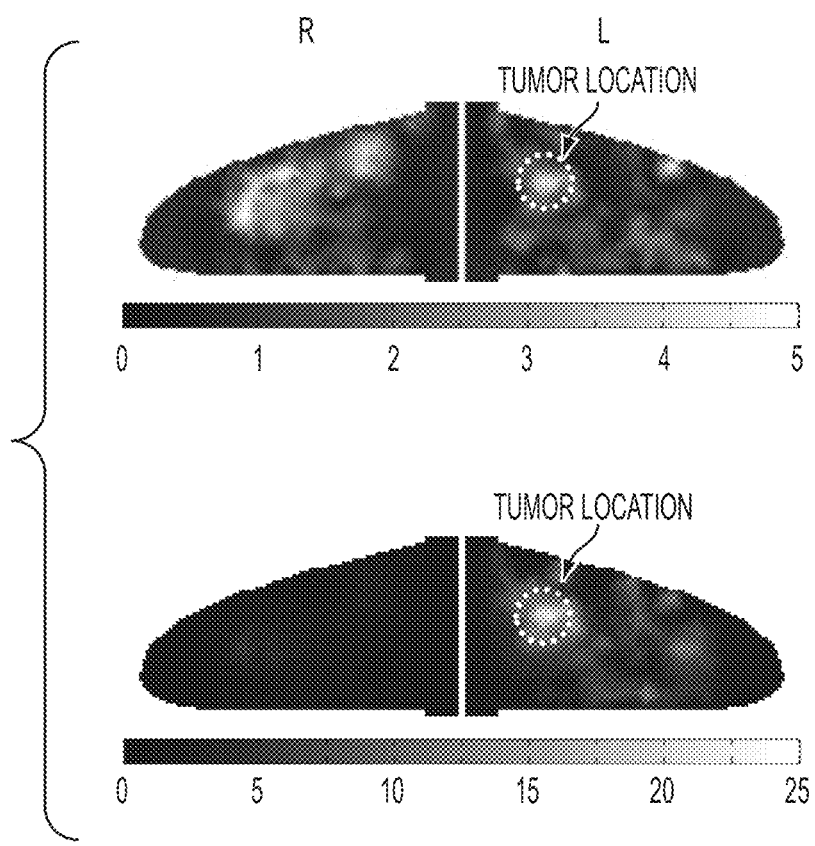
FIG. 6 shows sagittal transects obtained from the left (affected) and right (unaffected) breast for a subject with a 2 cm diameter tumor.

Still another consideration might be to employ a scheme wherein image features are expressed as a Z-score (the ratio of a deviation from the mean to the standard deviation), and image pixels exceeding some minimal value are identified as outliers. In its simplest form, this could be applied to each breast under consideration. A general concern with such an approach is the frequent existence of image outlier values in the vicinity of the surface optodes, regardless of whether an evoked response is elicited or not. An alternative approach would be to employ a referencing scheme wherein image-pixel values in one breast are symmetrically compared to those in the other. One challenge here is the knowledge that breast sizes typically vary bilaterally, and hence without careful consideration of such differences, comparisons of this sort are unlikely to be effective. Still another approach is to use the Z-scores obtained from one breast and compare these to the other. As with the description given for resting-state measures, conditions for data collection and analysis include: (1) imposition of substantially symmetric external boundary conditions, (2) collection of simultaneous bilateral dynamic measures, (3) referencing measures of one breast to another. Compared to the outlined resting-state measures, the principal difference applied to event-related maneuvers is simply the dimensionality of the reference factor (scalar vs. matrix) derived from the contralateral breast. It deserves emphasis that use of a matrix referencing technique such as considered here is not limited to univariate measures from which associated Z-scores can be derived. Bivariate and multivariate referencing schemes also can be applied. To those skilled in the art, this general approach is known as the Mahalanobis-distance method An example of the effectiveness of the considered approach is shown in FIG. 6. Shown in FIG. 6 are sagittal transects obtained from the left (affected) and right (unaffected) breast for a subject with a 2 cm diameter tumor. The images shown in the top row were computed by referencing each breast to itself using a Z-score method. The images in the bottom row were computed by referencing the unaffected breast to the affected breast, also using a Z-score method. Note that in the particular example shown here, the actual computed quantity was obtained using a two-component (totalHb, HbSat) Mahalanobis method. Inspection reveals two principal findings. First is that the difference in contrast features between the affected and unaffected breast are notably more apparent when a contralateral-reference approach (bottom row) is employed. Second, is that the amplitude of the contrast map in the affected breast is notably larger when this method is used.

It deserves emphasis that the considered methodology can also be applied to other forms of event-related maneuvers, such as can be accomplished using the articulation mechanism shown in FIG. 2. In such cases, it is important to employ a bilaterally symmetric articulation of the breasts and to allow sufficient time (typically 60 seconds) for the tissue to undergo the expected stress relaxation to the applied force such that the expected changes in optical pathlengths have stabilized.

Example 3: A Clinical Study with Multiple Maneuvers

We have conducted a clinical study using subjects having the demographic summary values identified in Table 6. Inspection reveals that members of each group have similar age and body-mass index (BMI) values. For each subject, optical time-series measures were obtained and subsequently analyzed using the steps outlined in Section 1. Results from this analysis were subjected to ROC analysis to determine the diagnostic discriminatory value of the individually derived group measures obtained during the baseline, articulation and respiratory-gas maneuver periods, and for a combined multivariate measure involving all three biometrics. In all cases, the ROC analysis results reported correspond to the combined results obtained from the healthy control and benign disease group compared to the cancer group.

TABLE 6

Subject Demographics

| Group | Number of Subjects | Age (years) (Mean ± SD) | BMI (Mean ± SD) |
| --- | --- | --- | --- |
| Cancer | 12 | 54.2 ± 11.1 | 32.3 ± 8.7 |
| Benign | 17 | 49.3 ± 9.2 | 33.4 ± 6.5 |
| Healthy | 12 | 55.2 ± 12.2 | 32.4 ± 3.8 |

Figure 7:
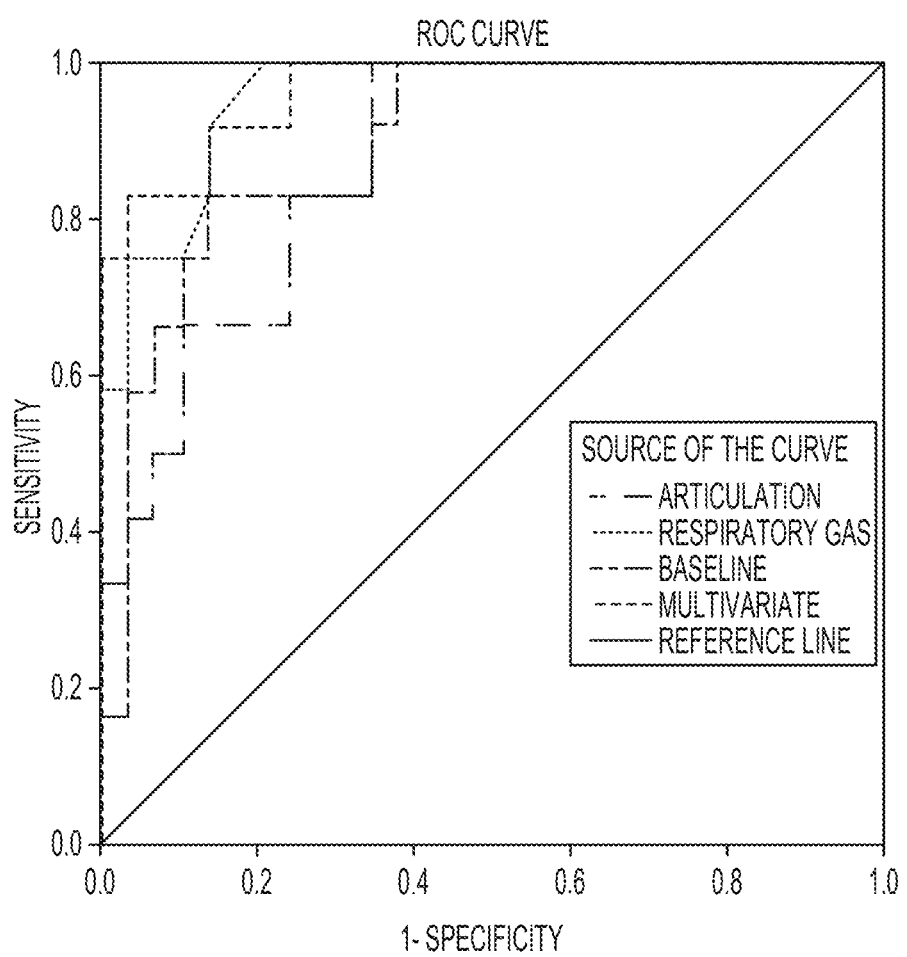
FIG. 7 shows ROC Profiles of individual biometrics, and of a composite biometric derived from application of binary logistic regression.

Shown in FIG. 7 are the ROC profiles obtained from each maneuver (baseline, articulation, respiratory gas), individually or in combination. The specific biometrics derived from each maneuver is the following:

Baseline Measurement:
Paired difference of the TMSSD metric derived from the reconstructed oxyhemoglobin signal.
Articulation Maneuver:
Ratio of the spatial standard deviation of deoxyhemoglobin values obtained from the sensor-array data (i.e., without image reconstruction) for the left breast (affected), divided by the corresponding value for the right breast (unaffected), following application of a 7.1 N medial-lateral articulation maneuver simultaneously to both breasts.

Respiratory Gas Maneuver:

Paired difference of the change in the spatial mean of the reconstructed HbSat value, following reaching a quasi-steady state while breathing 98% $O_2$, 2% $CO_2$, with respect to the HbSat value when breathing room air.

Shown in Table 7 is a summary of the computed AUCs for the ROC profiles shown in FIG. 7. Inspection verifies that the best performance is achieved using the multivariate metric.

TABLE 7

Area under the curve in FIG. 7

| Test Result Variable(s) | AUC (%) | Asymptotic Standard Error (%) | Asymptotic Sig. (p-value) | AUC Asymptotic 95% Confidence Interval (%) | |
|---|---|---|---|---|---|
| | | | | Lower Bound | Upper Bound |
| Articulation | 87.6 | 5.4 | <0.0005 | 77.2 | 98.1 |
| Respiratory Gas | 95.8 | 2.7 | <0.0005 | 90.5 | 100 |
| Baseline | 89.9 | 5.0 | <0.0005 | 80.2 | 99.7 |
| Multivariate | 96.6 | 2.6 | <0.0005 | 91.5 | 100 |

The capture of simultaneous measures affords the opportunity to recognize differences among the two breasts for the detection of cancer by considering elements of dissimilarity among the various elements of the hemoglobin signal. In the specific example shown in FIGS. 8-10, information from one breast is used as a reference to detect outliers in contrast features for the other breast. The approach taken requires consideration of at least two elements of the information space associated with the measurement data, and these elements can be derived from either the sensor or image space, or from both.

Figure 8:
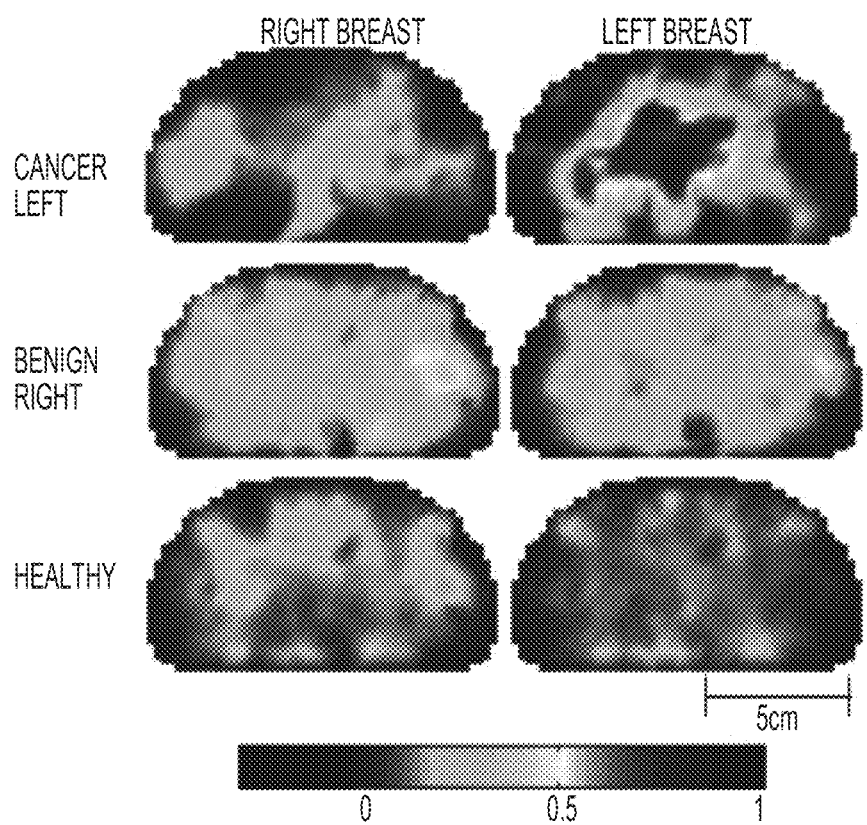
FIG. 8 shows coronal sections of change in hemoglobin oxygen saturation in response to a carbogen challenge. Images are normalized to their maximum value of all subjects.
Figure 9:
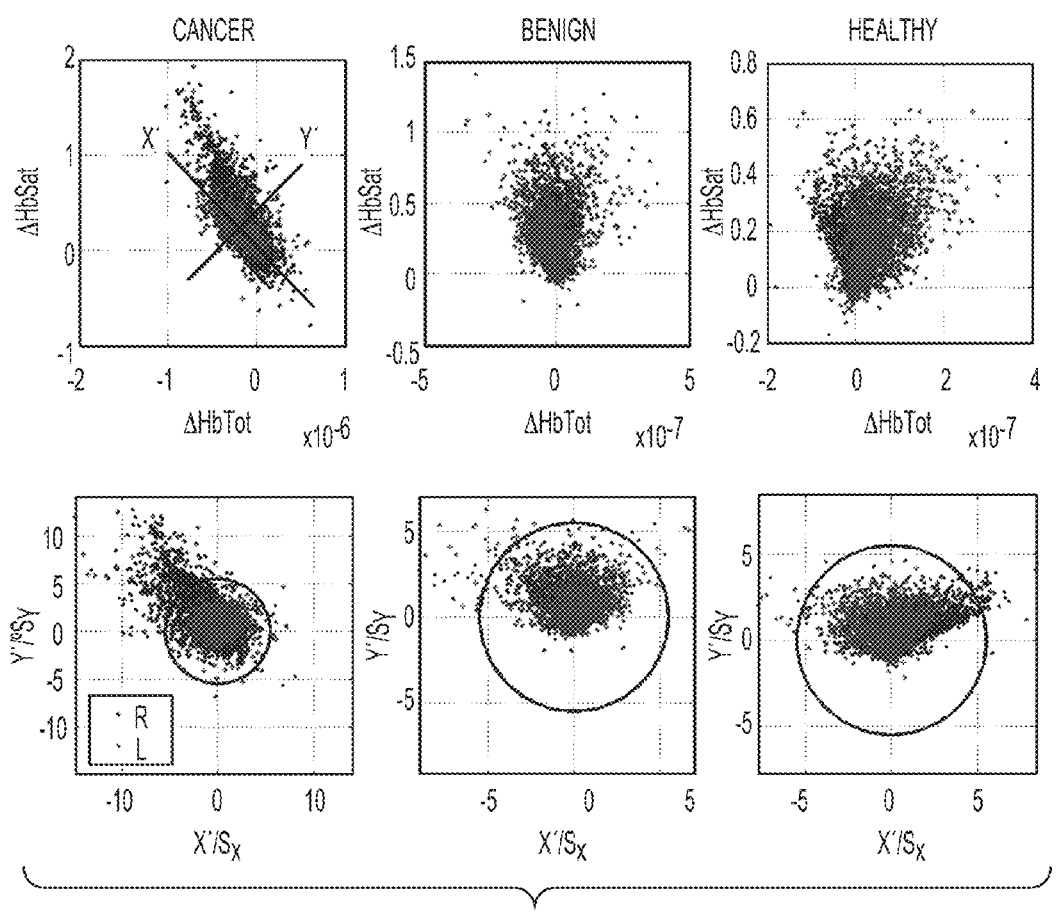
FIG. 9 includes graphs for the carbogen-induced change in HbSat vs. the change in HbTot (with respect to the baseline mean values), and for a linear transform i.e., (Mahalanobis distance) of the data in that permits straightforward evaluation of each data point's statistical distance from the mean (HbTot,HbSat) values. Circles show critical values for defining outliers.

Shown in FIG. 8 are images of the change in hemoglobin oxygen saturation for the left and right breasts, in response to application of carbogen, for individuals from the three different patient groups listed in Table 6. Present in the cancer subject's image is a large area of enhanced contrast. Inspection of the images obtained from the benign breast-pathology subject also reveals image features that, while having lower contrast, nevertheless are elevated compared to those for the healthy subject.

To distinguish which contrast features may or may not suggest the presence of a tumor, the Mahalanobis distance method has been applied to determine which features in one breast can be differentiated from the other. This is accomplished using the following steps.

Step 1. Using information obtained from two or more different features of the hemoglobin signal, generate a scatter plot of the paired image-pixel values for each respective breast. An example of this plot is shown in the upper half of FIG. 9 for oxygen saturation plotted against total hemoglobin.

Step 2. Transform the data to generate a normalized plot having a mean of zero and unit variance. This is accomplished by projecting the mean-subtracted totalHb and HbSat onto the eigenvectors of the totalHb-HbSat covariance matrix. Each resulting variable then is normalized to its standard deviation. An example of the transformed plot is shown in the lower half of FIG. 9.

Step 3. Specify a threshold beyond which identified pixels are considered statistical outliers (indicated circle, FIG. 9).

Figure 10:
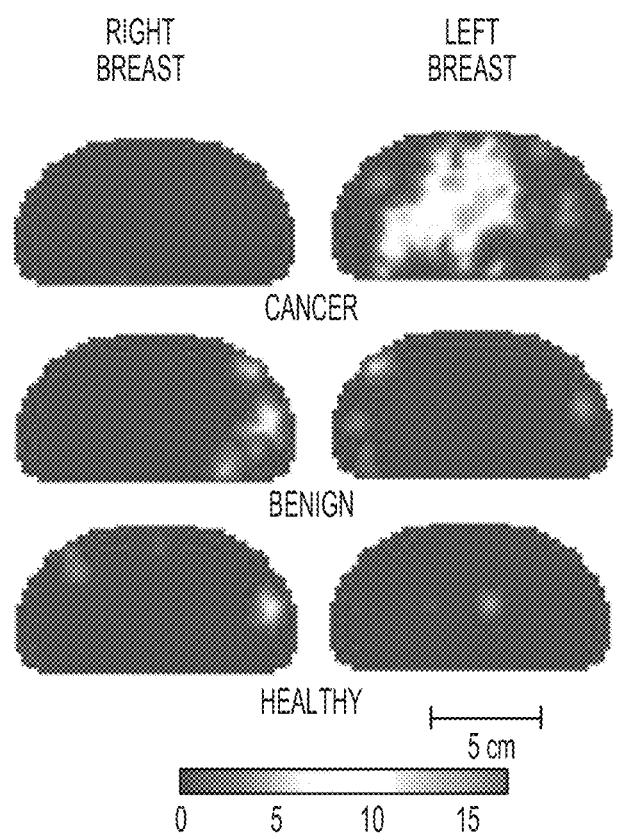
FIG. 10 shows coronal sections of statistical distance thresholded at 5.5 units. Images are normalized to their maximum value of all subjects. Same subjects have been used as in FIG. 8.

Step 4. Plot the pixels identified as outliers to generate a thresholded map for a selected element of the hemoglobin signal. FIG. 10 shows examples of the resulting maps when data in FIG. 8 was treated as outlined by applying Steps 1-4.

Inspection of the thresholded maps clearly identifies that essentially none of the image features seen in either the unaffected (right) breast from the cancer subject, or either breast from the benign breast pathology or healthy subjects, in FIG. 4 are identified as being statistically significant. Also revealed is a much improved distinction of the borders of image features that are associated with the tumor from the background (cf. FIGS. 8 and 10). The clear advantage of this approach is that by using information simultaneously recorded from both breasts, features mainly otherwise obscured can be readily identified in a statistically rigorous manner.

It deserves emphasis that the considered dissimilarity detection scheme, wherein an appropriate reference measure is available, can be applied to any form of imaging data. One application area where significant utility might be obtained is in the detection of mild head injuries. Here two or more features extracted from, for instance, structural MRI image data from the left hemisphere can serve as a reference for detecting subtle dissimilarities in information for the right hemisphere. Additionally, the indicated referencing approach could be further generalized to allow for detection of dissimilarities on a group level, wherein the considered reference is the computed Mahalanobis distance plot derived from measures obtained from a group of healthy individuals. Also, because detection of image subtleties holds advantages to other fields, the considered approach could be extended to explore other types of imaging studies outside of medical applications.

A working prototype apparatus embodying the present invention has been demonstrated. Advantages of the present invention include, but are not limited to:

(1) Providing for functional measures sensitive to the principal phenotypes of breast cancer.
(2) Employing non-ionizing radiation.
(3) Economical sensing hardware.
(4) Sensing measures are unaffected by breast density.
(5) No need for hard and painful compression as with x-ray mammography.

While the invention has been described in terms of specific embodiments, it is evident in view of the foregoing description that numerous alternatives, modifications and variations will be apparent to those skilled in the art. Each of the various embodiments of the present disclosure can be implemented alone, or in combination with any other embodiments of the present disclosure, unless expressly disclosed otherwise or otherwise impossible as would be known to one of ordinary skill in the art. Accordingly, the invention is intended to encompass all such alternatives, modifications and variations which fall within the scope and spirit of the invention and the following claims.

What is claimed is:

1. A system for detecting features within a pair of breasts, said system comprising:

a diffuse optical measurement system including at least one pair of optical sources and a pair of sensing heads configured to fit a pair of breasts and to simultaneously measure optical tomographical data from said pair of breasts while imposing bilaterally symmetric external boundary conditions for optical tomography upon said pair of breasts to form simultaneously measured optical tomographical data; and a computer configured to analyze said simultaneously measured optical tomographical data by running an automated program, wherein said automated program comprises steps of:

generating a reference data field as a function of space and measurement time based on a first subset of said simultaneously measured optical tomographical data on one of said pair of breasts;

performing a statistical analysis on a variation, from said reference data field, of a data field including said simultaneously measured tomographical data for another of said pair of breasts wherein a spatial standard deviation of the temporal mean (SSDTM) is obtained for a first breast and a second breast of the pair of breasts; and generating data that is indicative of a presence or absence of breast cancer in said another of said pair of breasts based on said statistical analysis, wherein the spatial standard deviation of the temporal mean (SSDTM) for the first breast is subtracted from the spatial standard deviation of the temporal mean (SSDTM) of the second breast to determine a paired difference value, wherein the presence of breast cancer is indicated by the paired difference value being above a threshold.

2. The system of claim 1, wherein said variation is measured for each pair of corresponding physical points that are present in said pair of breasts and are mapped to each other by a mirror symmetry in said bilaterally symmetric external boundary conditions.

3. The system of claim 2, wherein said statistical analysis includes an outlier analysis that identifies locations of physical points at which an absolute value of said variation is greater than a predefined multiple of a standard deviation of said variation.

4. The system of claim 1, wherein said generating of said reference data field comprises spatially averaging said simultaneously measured optical tomographical data or derived data therefrom across said pair of breasts.

5. The system of claim 1, wherein said generating of said reference data field as said function of space and measurement time is performed employing said simultaneously measured optical tomographical data, without employing data generated from any other physical breast than said pair of breasts or from any model for a physical breast.

6. The system of claim 1, wherein said pair of sensing heads is configured to provide a bilaterally symmetric articulation while measuring said optical tomographical data, wherein said pair of sensing heads maintain said mirror symmetry.

7. The system of claim 1, wherein said simultaneously measured optical tomographical data comprises data on hemodynamic response or vascular tone.

8. The system of claim 1, wherein said simultaneously measured optical tomographical data comprises an oxyhemoglobin level and a deoxyhemoglobin level.

9. The system of claim 8, wherein said reference data field comprises at least one of:
a total hemoglobin level;
a hemoglobin oxygen saturation; and
a measure of hemoglobin oxygen extraction efficiency.

10. The system of claim 1, wherein said system further comprises a means for altering a composition of a respiratory gas supplied to a patient from whom said optical tomographical data is simultaneously measured.

11. A method of detecting features within a pair of breasts comprising:

mounting at least one pair of optical sources and a pair of sensing heads of a diffuse optical measurement system to fit a pair of breasts of a patient;

simultaneously measuring optical tomographical data from said pair of breasts while imposing bilaterally symmetric external boundary conditions for optical tomography upon said pair of breasts to form simultaneously measured optical tomographical data;

analyzing said simultaneously measured optical tomographical data by running an automated program on a computing means, wherein said automated program comprises steps of:

generating a reference data field as a function of space and measurement time based on a first subset of said simultaneously measured optical tomographical data on one of said pair of breasts;

performing a statistical analysis on a variation, from said reference data field, of a data field including said simultaneously measured tomographical data for another of said pair of breasts, wherein a spatial standard deviation of the temporal mean (SSDTM) is obtained for a first breast and a second breast of the pair of breasts; and generating data that is indicative of a presence or absence of breast cancer in said another of said pair of breasts based on said statistical analysis, wherein the spatial standard deviation of the temporal mean (SSDTM) for the first breast is subtracted from the spatial standard deviation of the temporal mean (SSDTM) of the second breast to determine a paired difference value, wherein the presence of breast cancer is indicated by the paired difference value being above a threshold.

12. The method of claim 11, wherein said variation is measured for each pair of corresponding physical points that are present in said pair of breasts and are mapped to each other by a mirror symmetry in said bilaterally symmetric external boundary conditions.

13. The method of claim 12, wherein said statistical analysis includes an outlier analysis that identifies locations of physical points at which an absolute value of said variation is greater than a predefined multiple of a standard deviation of said variation.

14. The method of claim 11, wherein said generating of said reference data field comprises spatially averaging said simultaneously measured optical tomographical data or derived data therefrom across said pair of breasts.

15. The method of claim 11, wherein said generating of said reference data field as said function of space and measurement time is performed employing said simultaneously measured optical tomographical data, without employing data generated from any other physical breast than said pair of breasts or from any model for a physical breast.

16. The method of claim 11, further comprising providing a bilaterally symmetric articulation while measuring said optical tomographical data, wherein said pair of sensing heads maintain said mirror symmetry.

17. The method of claim 11, wherein said simultaneously measured optical tomographical data comprises data on hemodynamic response or vascular tone.

18. The method of claim 11, wherein said optical tomographical data is measured under a condition of a resting state.

19. The method of claim 11, wherein said optical tomographical data is measured after inducing an evoked change in cardiovascular tone or cardiovascular functionality of said patient.

20. The method of claim 11, further comprising altering a composition of a respiratory gas supplied to a patient from whom said optical tomographical data is simultaneously measured.

* * * * *